(12) United States Patent
Guo et al.

(10) Patent No.: US 9,511,169 B2
(45) Date of Patent: Dec. 6, 2016

(54) MEDICAL DEVICES CONTAINING DRY SPUN NON-WOVENS OF POLY-4-HYDROXYBUTYRATE AND COPOLYMERS WITH ANISOTROPIC PROPERTIES

(71) Applicant: Tepha, Inc., Lexington, MA (US)

(72) Inventors: Kai Guo, Waltham, MA (US); Fabio Felix, Foxborough, MA (US); David P. Martin, Arlington, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

(21) Appl. No.: 14/279,665

(22) Filed: May 16, 2014

(65) Prior Publication Data

US 2015/0012018 A1    Jan. 8, 2015

Related U.S. Application Data

(63) Continuation-in-part of application No. 13/160,942, filed on Jun. 15, 2011.

(60) Provisional application No. 61/354,994, filed on Jun. 15, 2010.

(51) Int. Cl.
*A61L 27/18* (2006.01)
*D04H 1/42* (2012.01)
(Continued)

(52) U.S. Cl.
CPC .............. *A61L 27/18* (2013.01); *A61L 27/54* (2013.01); *A61L 29/06* (2013.01); *A61L 29/16* (2013.01); *A61L 31/06* (2013.01); *A61L 31/16* (2013.01); *D04H 1/42* (2013.01); *D04H 1/435* (2013.01); *D04H 1/4382* (2013.01); *D04H 1/56* (2013.01); *D04H 1/76* (2013.01); *D04H 3/11* (2013.01); *D04H 3/16* (2013.01); *Y10T 442/60* (2015.04)

(58) Field of Classification Search
USPC .................. 424/1.11, 9.1; 442/334; 428/220; 264/115; 623/11.11
See application file for complete search history.

(56) References Cited

U.S. PATENT DOCUMENTS 5,811,272 A    9/1998 Snell
6,245,537 B1    6/2001 Williams
(Continued)

FOREIGN PATENT DOCUMENTS

EP    0628586    12/1994
EP    2505213    10/2012
(Continued)

OTHER PUBLICATIONS

Duvernoy, et al. "A biodegradable patch used as a pericardial substitute after cardiac surgery: 6- and 24-month evaluation with CT", Thorac. Cardiovacs. Surgeon, 43:271-274 (1995).
(Continued)

*Primary Examiner* — Lynda Salvatore
(74) *Attorney, Agent, or Firm* — Pabst Patent Group LLP

(57) ABSTRACT

Continuous processing methods are used for making absorbable polymeric non-wovens, with anisotropic properties, improved mechanical properties and without substantial loss of polymer molecular weight during processing. The method includes producing dry spun-non wovens from a polymer, and collecting the fibers using a rotating collector plate, preferably a rotating cylinder, to collect the non-woven instead of a fiberglass stationary collector plate. The non-wovens can be used for a variety of purposes including fabrication of medical devices.

17 Claims, 1 Drawing Sheet

(51) Int. Cl.

| | | |
|---|---|---|
| A61L 27/54 | (2006.01) | |
| A61L 29/06 | (2006.01) | |
| A61L 29/16 | (2006.01) | |
| A61L 31/06 | (2006.01) | |
| A61L 31/16 | (2006.01) | |
| D04H 1/56 | (2006.01) | |
| D04H 3/16 | (2006.01) | |
| D04H 1/435 | (2012.01) | |
| D04H 1/76 | (2012.01) | |
| D04H 3/11 | (2012.01) | |
| D04H 1/4382 | (2012.01) | |

(56) References Cited

U.S. PATENT DOCUMENTS

| | | |
|---|---|---|
| 6,316,262 B1 | 11/2001 | Huisman |
| 6,323,010 B1 | 11/2001 | Skraly |
| 6,548,569 B1 * | 4/2003 | Williams ............ C08K 5/0033 521/27 |
| 6,555,123 B2 | 4/2003 | Williams |
| 6,585,994 B2 | 7/2003 | Williams |
| 6,610,764 B1 | 8/2003 | Martin |
| 6,623,748 B2 | 9/2003 | Clokie |
| 6,828,357 B1 | 12/2004 | Martin |
| 6,838,493 B2 | 1/2005 | Williams |
| 6,867,247 B2 | 3/2005 | Williams |
| 6,867,248 B1 | 3/2005 | Martin |
| 6,878,758 B2 | 4/2005 | Martin et al. |
| 6,905,987 B2 | 6/2005 | Noda |
| 7,025,980 B1 | 4/2006 | Williams |
| 7,179,883 B2 | 2/2007 | Williams |
| 7,244,442 B2 | 7/2007 | Williams |
| 7,268,205 B2 | 9/2007 | Williams |
| 8,287,909 B2 * | 10/2012 | Martin ............... A61L 15/26 424/402 |
| 8,431,060 B2 | 4/2013 | Huang |
| 2003/0211131 A1 | 11/2003 | Martin |
| 2005/0158542 A1 | 7/2005 | Iwata |
| 2009/0012604 A1 | 1/2009 | Schmitz |
| 2009/0162276 A1 | 6/2009 | Martin |
| 2011/0236974 A1 | 9/2011 | Ogle |
| 2012/0150285 A1 | 6/2012 | Cahil |

FOREIGN PATENT DOCUMENTS

| | | |
|---|---|---|
| WO | 9523249 | 8/1995 |
| WO | 9932536 | 7/1999 |
| WO | 0056376 | 9/2000 |
| WO | 2004101002 | 11/2004 |
| WO | 2006015276 | 2/2006 |
| WO | 2007092464 | 8/2007 |
| WO | 2009085823 | 7/2009 |
| WO | 2011106205 | 9/2011 |

OTHER PUBLICATIONS

Hori, et al., "Chemical synthesis of high molecular weight poly(3-hydroxybutyrate-co-4-hydroxybutyrate)", Polymer 36:4703-4705 (1995).

Houk, et al., "Why delta-valerolactone polymerizes and gamma-butyrolactone does not", J. Org. Chem., 73 (7), 2674-2678 (2008).

Martin and Williams, "Medical Applications of Poly-4-hydroxybutyrate: A Strong Flexible Absorbable Biomaterial", Biochem. Eng. J., 16:97-105 (2003).

Steinbüchel, et al., "Diversity of Bacterial Polyhydroxyalkanoic Acids", FEMS Microbial. Lett., 128:219-228 (1995).

Williams, et al., "Applications of PHAs in Medicine and Pharmacy, in Biopolymers", Polyesters, III, 4:91-127 (2002).

* cited by examiner

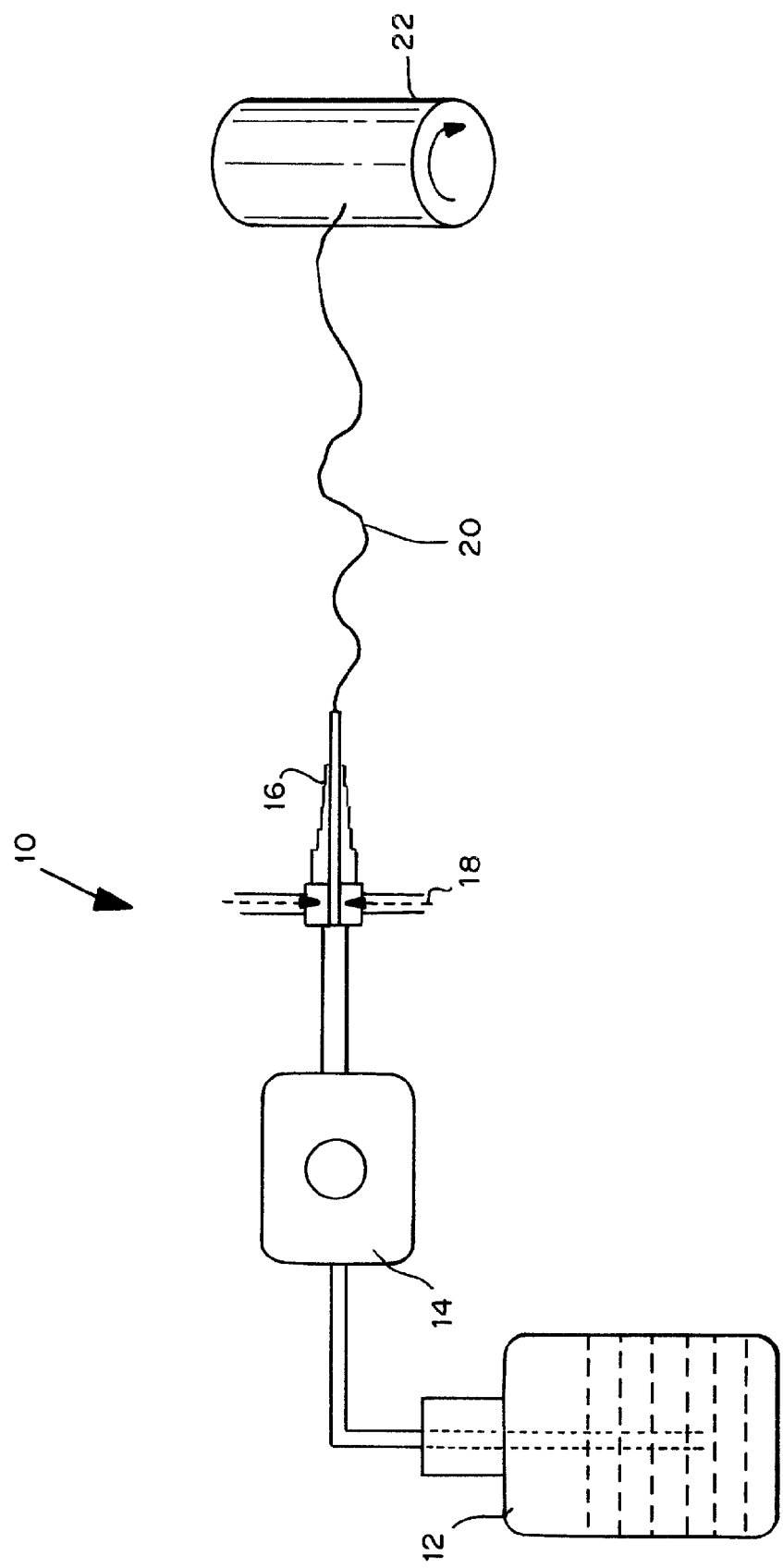

MEDICAL DEVICES CONTAINING DRY SPUN NON-WOVENS OF POLY-4-HYDROXYBUTYRATE AND COPOLYMERS WITH ANISOTROPIC PROPERTIES

CROSS-REFERENCE TO RELATED APPLICATIONS

This application claims the benefit of priority to U.S. Ser. No. 13/160,942 filed Jun. 15, 2011, and of U.S. Ser. No. 61/354,994, filed on Jun. 15, 2010; the disclosures of these applications are incorporated herein by reference.

FIELD OF THE INVENTION

The present invention generally relates to polymeric compositions that can be processed into dry spun non-wovens using continuous processes. The compositions include polymers or copolymers comprising 4-hydroxybutyrate, and can be processed into non-wovens that have high burst strength, and retain polymer molecular weight.

BACKGROUND OF THE INVENTION

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate (P4HB, Tepha-FLEX® biomaterial) is a strong, pliable thermoplastic polyester that, despite its biosynthetic route, has a relatively simple structure.

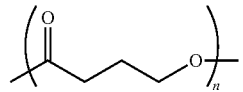

The polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128:219-228 (1995)).

U.S. Pat. Nos. 6,245,537, 6,623,748 and 7,244,442 describe methods of making PHAs with little to no endotoxin, which is suitable for medical applications. U.S. Pat. Nos. 6,548,569, 6,838,493, 6,867,247, 7,268,205, and 7,179,883 describe use of PHAs to make medical devices. Copolymers of P4HB include 4-hydroxybutyrate copolymerized with 3-hydroxybutyrate or glycolic acid (U.S. patent application No. 2003/0211131 by Martin and Skraly, U.S. Pat. No. 6,316,262 to Huisman et al., and U.S. Pat. No. 6,323,010 to Skraly, et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams, et al. and WO 99/32536 to Martin, et al. Applications of P4HB have been reviewed in Williams, et al., *Polyesters, III*, 4:91-127 (2002), and by Martin, et al. "Medical Applications of Poly-4-hydroxybutyrate: A Strong Flexible Absorbable Biomaterial", *Biochem. Eng. J.* 16:97-105 (2003). Medical devices and applications of P4HB have also been disclosed by WO 00/56376 to Williams, et al.

Several patents including U.S. Pat. Nos. 6,555,123, 6,585,994, and 7,025,980 describe the use of PHAs in tissue repair and engineering.

In the practice of surgery there currently exists a need for absorbable non-wovens with improved performance. These non-wovens can be used, for example, for soft tissue repair, to reinforce tissue structures, to separate tissues, and to serve as tissue engineering scaffolds, including guided tissue regeneration scaffolds. They may also be used as components of other devices. A number of other absorbable materials have been used to produce non-wovens for use in surgery. For example, non-wovens have been made from polyglycolic acid (PGA) or copolymers containing lactic acid. These materials do not, however, have ideal properties for many procedures and applications. Non-wovens made from polyglycolic acid breakdown too rapidly for many applications, and release acidic degradation products that can cause inflammatory reactions.

WO 04/101002 to Martin et al. discloses monofilament and multifilament knitted meshes of P4HB, produced by knitting monofilament and multifilament fibers of P4HB. WO 09/085823 to Ho, et al. discloses medical devices containing melt-blown non-wovens of poly-4-hydroxybutyrate and copolymers thereof. U.S. Pat. No. 8,287,909 discloses non-wovens of poly-4-hydroxybutyrate derived by a continuous melt-blown process. Notably, the process of melt blowing can limit the utility of this method to produce non-wovens, particularly when it is necessary to produce three-dimensional non-woven fabrics and devices, and apply coatings of non-wovens on scaffolds or other materials. The process of melt extrusion causes a dramatic loss in the molecular weight of the polymer such that the molecular weight of the polymer in the melt blown non-woven is substantially less than in the polymer feed. The lower molecular weight of melt blown non-woven is a particular disadvantage when it is desirable to retain mass and/or mechanical properties, such as burst strength, in vivo, for a prolonged period of time, since lower molecular weight P4HB non-wovens degrade faster in vivo than higher molecular weight P4HB non-wovens. U.S. Publication No. 2012/0150285 by Cahil, et al. discloses a continuous process for making dry spun non-wovens, including non-wovens of P4HB. The non-wovens are collected on a stationary plate.

There is still a need for non-wovens of P4HB, with improved mechanical properties, which retain the higher molecular weight of the starting material, burst strength, and degradation kinetics.

It is an object of the present invention to provide methods to produce dry spun non-wovens of absorbable P4HB and copolymers thereof with improved mechanical properties, and without substantial loss of the polymer molecular weight during processing.

It is another object of the present invention to provide dry spun non-wovens which are biocompatible and can be used in medical applications, for example, as implants such as devices for soft tissue repair, replacement, and regeneration, temporary tissue support, tissue separation, as well as devices or components of devices for tissue in-growth (or guided tissue regeneration) and tissue engineering.

It is therefore an object of the invention to provide continuous processes for dry spun non-woven production, which can be incorporated into or formed into medical devices with excellent physical and mechanical properties for medical applications.

SUMMARY OF THE INVENTION

Continuous processing methods for making absorbable polymeric non-wovens, with anisotropic properties, improved mechanical properties and without substantial loss of polymer molecular weight during processing, with one or more of the following properties: burst strength greater than 0.001 Kgf, high toughness, low modulus, high molecular weight, and thickness from 10 µm to 10 mm, have been developed. The ratio of the tensile strength in the machine direction to the tensile strength in the cross direction is greater than 1.2. A melt blown non-woven would need to have 2-3 times the areal density of a dry spun non-woven to be of comparable burst strength. Alternatively, the dry spun non-woven has a burst strength that is 2-3 times higher than that of a melt blown non-woven with similar areal density. The non-wovens have unexpectedly good cohesion of the fibers in the non-wovens due to fusion of the fibers, which remain tacky, during the web collection process.

The method includes producing dry spun-non wovens from a polymer, and collecting the fibers using a rotating collector plate, preferably a rotating cylinder, to collect the non-woven instead of a stationary collector plate. The speed and/or circumference of the rotating collector plate may be varied in order to select the properties desired in the machine direction relative to the cross direction. In a preferred embodiment, the speed of the rotating collector plate is 10 rpm, more preferably greater than 50 rpm, and even more preferably greater than 100 rpm. The distance between the spray gun nozzle and the rotating collector plate is preferably between 20 inches and 40 inches. In some embodiments, the rotating collector plate is a cylinder. In these embodiments, the diameter of the rotating cylinder is between 0.25 inches and 6 inches, and the width of the rotating cylinder is between 6 inches and 20 inches. Wider collectors may also be used if a plurality of spray nozzles is used. The time required to collect the nonwoven on the rotating collector plate will depend upon the desired thickness of the nonwoven and configuration of the nonwoven, capacity of the spray gun assembly, concentration of the polymer solution, choice of solvent, temperature, nozzle diameter(s), and the pressure of the compressed air. This process aligns the fibers forming the non-woven, resulting in a stronger materials.

In the preferred embodiment, the polymer is a polyhydroxyalkanoate, more preferably a polymer comprising 4-hydroxybutyrate, most preferably a 4-hydroxybutyrate homopolymer or copolymer thereof. A particularly preferred embodiment is a non-woven of poly-4-hydroxybutyrate homopolymer or copolymer thereof, wherein the non-woven comprises fine fibers with average diameters between 0.01 µm and 50 µm, wherein the non-woven is derived by dry spun processing, and wherein a solution of the polymer is injected into a stream of high velocity gas with a pressure of between 1 and 500 psi for solvent stripping and polymer strand attenuation. The weight average molecular weight of the poly-4-hydroxybutyrate or copolymer thereof decreases less than 20% during the processing of the polymer or copolymer.

These can be used for a variety of purposes including fabrication of medical devices.

BRIEF DESCRIPTION OF THE DRAWINGS

FIG. 1 is a diagram of the process to manufacture dry spun non-woven materials from poly-4-hydroxybutyrate and copolymers thereof.

DETAILED DESCRIPTION OF THE INVENTION

Definitions

"Anisotrophic", as used herein, refers to a material formed of polymeric fibers which are aligned, irregardless of the orientation of the polymer in the fibers. Alignment of the fibers improves the mechanical properties of the resulting material, such as a non-woven fabric.

"Oriented", as used herein, refers to alignment of the polymer molecules in a polymeric material. Alignment of the polymer molecules can improve polymer properties such as tensile and/or burst strength.

"Poly-4-hydroxybutyrate", as generally used herein, means a homopolymer of 4-hydroxybutyrate units. It may be referred to herein as P4HB or TEPHAFLEX® biomaterial (manufactured by Tepha, Inc., Lexington, Mass.).

"Copolymers of poly-4-hydroxybutyrate", as generally used herein, means any polymer comprising 4-hydroxybutyrate with one or more different hydroxy acid units.

"Bicomponent", as generally used herein, means a non-woven comprising two materials.

"Blend", as generally used herein, means a physical combination of different polymers, as opposed to a copolymer comprised of two or more different monomers.

"Burst strength", as used herein, is determined by test method ASTM D6797-02 "Standard test method for bursting strength of fabrics constant rate of extension (CRE) ball burst test," using a MTS Q-Test Elite universal testing machine, or similar device. The testing fixture uses a one-inch diameter ball and a 1.75-inch diameter circular opening. Non-woven samples are tested with a pre-load setting of 0.05 Kg, and a ball rate of 305 mm/minute until failure. This method may be modified to use a smaller (ex. ⅜") rounded probe for testing samples of smaller sizes, such as might be used in a medical device or implanted in a small animal like a rabbit or a rat. However, the smaller ⅜" fixture typically results in lower burst values for the same material when compared to testing performed with a 1" ball. As a result, the burst value for a material tested using a ⅜" probe is typically 48% of the value measured using the 1" probe.

"Tensile modulus" is the ratio of stress to strain for a given material within its proportional limit.

"Toughness" means a property of a material by virtue of which it can absorb energy; the actual work per unit volume or unit mass of material that is required to rupture it. Toughness is usually proportional to the area under the load-elongation curve such as the tensile stress-strain curve. (Rosato's Plastics Encyclopedia and Dictionary, Oxford Univ. Press, 1993)

"Elongation" or extensibility of a material, means the amount of increase in length resulting from, as an example, the tension to break a specimen. It is expressed usually as a percentage of the original length. (Rosato's Plastics Encyclopedia and Dictionary, Oxford Univ. Press, 1993)

"Molecular weight", as used herein, unless otherwise specified, refers to the weight average molecular weight (Mw), not the number average molecular weight (Mn), and is measured by GPC relative to polystyrene.

"Absorbable" as generally used herein means the material is broken down in the body and eventually eliminated from the body within five years.

"Biocompatible" as generally used herein means the biological response to the material or device being appropriate for the device's intended application in vivo. Any metabolites of these materials should also be biocompatible.

"Area density" is also known as areal density, surface density, or superficial density. The area density of a two-dimensional object is calculated as the mass per unit area.

I. Compositions

Methods have been developed to produce medical devices comprising non-wovens of P4HB and copolymers thereof with improved mechanical properties. These methods may be used to prepare non-wovens with fine fibers having average diameters between 0.01 μm and 50 μm. A major advantage of the method over melt blown processing is that the molecular weight of the polymer may decrease less than 20% of its original value during dry spun processing. In addition, a major advantage over prior dry spun methods is that collecting the fibers on a moving or rotating collector instead of a stationary plate improves the mechanical properties of the non-woven (for example, tensile strength).

A. Polymers

The processes described herein can typically be used with poly-4-hydroxybutyrate (P4HB) or a copolymer thereof. Copolymers include polymers of 4HB with other hydroxyacid(s), such as 3-hydroxybutyrate, and polymers of 4HB with glycolic acid or lactic acid monomer. P4HB and copolymers thereof can be obtained from Tepha, Inc. of Lexington, Mass.

In a preferred embodiment, the P4HB homopolymer and copolymers thereof have a molecular weight, Mw, within the range of 50 kDa to 1,200 kDa (by GPC relative to polystyrene) and more preferably between 100 kDa and 600 kDa.

If desired, the PHA polymers may be blended or mixed with other materials prior to dry spinning. In a particularly preferred embodiment, P4HB and/or its copolymers may be blended with other absorbable polymers. Examples of other absorbable polymers include, but are not limited to, polymers comprising glycolic acid, lactic acid, 1,4-dioxanone, trimethylene carbonate, 3-hydroxybutyric acid, and caprolactone, including polyglycolic acid, polylactic acid, polydioxanone, polycaprolactone, copolymers of glycolic and lactic acids, polyglycolic acid:trimethylene carbonate polymers, copolymers of glycolide and ε-caprolactone, and copolymers of lactide and ε-caprolactone. The ratio of the PHA polymer in the blend to the non-PHA polymer component(s) may be varied in order to select the desired properties of the dry spun non-woven.

B. Non-Wovens

In a preferred embodiment, non-wovens can be prepared with a thickness of less than 10 mm, but greater than 10 μm. More preferably the thickness is between 50 μm and 3 mm. It has been discovered that non-wovens of P4HB polymer or copolymers thereof can be prepared by dry spinning with unexpectedly high retention of polymer molecular weight, high burst and tensile strengths. Notably, the molecular weight of the polymer decreases less than 20% during dry spinning. In a preferred embodiment, the poly-4-hydroxybutyrate or copolymer has a weight average molecular weight greater than 50 kDa relative to polystyrene. In a more preferred embodiment, the non-woven poly-4-hydroxybutyrate or copolymer has a weight average molecular weight greater than 210 kDa relative to polystyrene.

In contrast, non-wovens of P4HB or copolymers thereof prepared by melt blowing typically lose a significant amount of the polymer's initial molecular weight during melt processing. This results in a non-woven with significantly reduced molecular weight. WO 09/085823 to Ho, et al., for example, describes methods to produce non-wovens of P4HB and copolymers thereof by melt processing wherein the polymer loses up to 50% of the polymer's initial molecular weight.

Burst strength of the non-wovens can be determined by ASTM D6797-02, Standard Test Method for Bursting Strength of Fabrics Constant-Rate-of-Extension (CRE) Ball Burst Test. The testing fixture comprises a 1-inch diameter ball, and a fixture with a 1.75-inch diameter circular opening. This method may be modified to use a smaller (ex. ⅜") rounded probe for testing samples of smaller sizes, such as might be used in a medical device or implanted in a small animal like a rabbit or a rat. However, the smaller ⅜" fixture typically results in lower burst strength values for the same material when compared to testing performed with a 1" ball. As a result, the burst value for a material tested using a ⅜" probe is typically 48% of the value measured using the 1" probe. The non-woven samples are tested using a universal testing machine, for example, a Q-Test Elite by MTS, with a pre-load setting of 0.05 Kg, and a ball rate set at 305 mm/minute until failure. The ball or probe is pushed through the sample at a constant rate and force, and the load (Kgf) versus displacement (mm) curve is recorded. Breaking load (Kgf), elongation at break (mm) and location of break are recorded.

The non-wovens produced according to the methods described herein have high burst strengths and improved fusion of the fibers at their crossover points. Burst strengths exceed 0.001 Kgf, and more preferably exceed 0.01 Kgf when using a ⅜" ball burst fixture. For example, a dry spun non-woven of P4HB with an areal density of 13.3 g/m$^2$ has a burst strength of 0.75 Kgf using a ⅜" ball burst fixture. In comparison, a melt blown non-woven produced by the method of WO 09/085823 to Ho et al., with an areal density that is 2.9 times higher than the areal density of the non-wovens produced as described herein (i.e., an areal density of 38.5 g/m$^2$), has a burst strength that is only about 2 times higher (i.e. 1.55 Kgf) when using a 1" fixture. This translates to 0.74 Kgf if tested using a ⅜" probe.

C. Other Components

The P4HB polymer and copolymer dry spun non-wovens may contain other materials, including plasticizers, nucleants, other polymers, additives, dyes, and compatibilizers. Examples of plasticizers are disclosed by U.S. Pat. No. 6,905,987 to Noda et al. Other components may be added to impart benefits such as, but not limited to, increased stability, including oxidative stability, brightness, color, flexibility, resiliency, workability, processibility (by addition of processing aids), and viscosity modifiers.

In addition to adding other components directly to the P4HB polymer or copolymer thereof, it is also possible to prepare bicomponent non-wovens of P4HB or its copolymers. These bicomponent non-wovens can be prepared by dry spinning at least two polymers simultaneously, either from the same solution or from separate spinning nozzles. Additionally, layered structures may be created by first spinning one type of polymer (or mixture) and then spinning another, or spinning from different directions.

Active components, including therapeutic, diagnostic and/or prophylactic agents, or other substances may be incorporated into the non-wovens, either at the time of dry spinning, or in a later processing step. Such compositions may be used for controlled release of the drugs or other substances. These may be proteins, peptides, sugars, polysaccharides, glycoproteins, lipids, lipoproteins, nucleic acid molecules, inorganic or organic synthetic molecules, or combinations thereof. The non-wovens may comprise cells, proteins, or other substances including allograft and xenograft materials.

The non-woven may include one or more additional polymers such as a polymer of glycolic acid, lactic acid, 1,4-dioxanone, trimethylene carbonate, caprolactone and combinations thereof.

The non-woven may further including additives such as plasticizers, nucleants, compatibilizers, porogens, radiolabelled substances, imaging agents, radiopaque markers, contrast agents, anti-oxidants, dyes, viscosity modifiers, and odor control agents. For certain applications it may also be desirable to incorporate fillers, including materials such as titanium dioxide, calcium carbonate, hydroxyapatite, and tricalcium phosphate.

D. Devices

Non-wovens made from P4HB polymers and copolymers thereof by dry spun processes are characterized by their formation from fine fibers with average diameters ranging from 0.01 µm to 50 µm. Notably, the dry spun non-wovens may be produced with smaller fibers than the melt-blown non-wovens. The dry spun non-wovens are also characterized by their high burst and tensile strengths, exceeding 0.001 Kgf, and molecular weights within 20% of the value of the polymer from which they are derived. These non-wovens have properties that are substantially improved for many medical applications relative to PGA-based non-wovens. Because these dry spun non-wovens can be produced without substantial loss of molecular weight, they can also have significant advantages over melt-blown non-wovens. This is of particular significance where it is desirable for a non-woven material to retain its integrity and strength in vivo for a longer period of time. For example, in tissue engineering it may be desirable for a non-woven scaffold to be present in vivo for a prolonged period of time to allow tissue in-growth and tissue maturation before the scaffold is absorbed. Premature absorption of the scaffold will result in immature tissue formation, and potentially failure of the implant device. Thus, because dry spun non-wovens can be prepared without substantial loss of polymer molecular weight, and the body requires longer periods of time to degrade P4HB and copolymers thereof of higher molecular weight, a dry spun non-woven will remain in vivo as a scaffold for longer than a melt blow non-woven.

The non-wovens possess properties that are desirable in preparing medical products, particularly implantable medical devices. For example, the non-wovens may be used to make partially or fully absorbable biocompatible medical devices, or components thereof. Representative devices include stents, stent grafts, stent coatings, drug delivery devices, devices for temporary wound or tissue support, repair patches, tissue engineering scaffolds, retention membranes, anti-adhesion membranes, tissue separation membranes, hernia repair devices, hernia meshes, hernia plugs, laminated knitted or woven devices, device coatings, cardiovascular patches, vascular closure devices, slings, devices for pelvic floor reconstruction, bladder repair devices, biocompatible coatings, rotator cuff repair devices, meniscus repair devices, adhesion barriers, guided tissue repair/regeneration devices, articular cartilage repair devices, nerve guides, tendon repair devices, ligament repair devices, rotator cuff devices, meniscus repair devices, articular cartilage repair devices, osteochondral repair devices, intracardiac septal defect repair devices, atrial septal defect repair devices, PFO (patent foramen ovale) closure devices, left atrial appendage (LAA) closure devices, pericardial patches, bulking agents, filling agents, vein valves, heart valves, vascular grafts, myocardial regeneration devices, anastomosis devices, bone marrow scaffolds, meniscus regeneration devices, ligament and tendon grafts, ocular cell implants, spinal fusion devices, imaging devices, skin substitutes, dural substitutes, bone graft substitutes, wound dressings, bandages, wound healing devices, burn dressings, ulcer dressings, skin substitutes, hemostats, plastic surgery devices, breast lift devices, mastopexy devices, breast reconstruction devices, breast augmentation devices (including devices for use with breast implants), breast reduction devices (including devices for removal, reshaping and reorienting breast tissue), devices for breast reconstruction following mastectomy with or without breast implants, facial reconstructive devices, forehead lift devices, brow lift devices, eyelid lift devices, face lift devices, rhytidectomy devices, thread lift devices (to lift and support sagging areas of the face, brow and neck), rhinoplasty devices, devices for malar augmentation, otoplasty devices, neck lift devices, mentoplasty devices, cosmetic repair devices, and devices for facial scar revision.

II. Methods of Manufacturing Non-Wovens

Methods have been developed to produce medical devices comprising non-wovens of P4HB and copolymers thereof with high burst and tensile strength. These methods may be used to prepare non-wovens with fine fibers ranging in average diameter from 0.01 µm to 50 µm. The methods may be run continuously, which is particularly advantageous in manufacturing. These non-wovens are prepared by dry spinning A major advantage of the method over melt blown processing is that the molecular weight of the polymer may decrease less than 20% of its original value during dry spun processing. Due to the low processing temperature, the dry spinning approach can have other advantages over melt spinning, particularly in cases where the spinning mixture contains thermally sensitive materials, such as drugs, polymer or other additive. In these cases it may be possible to reduce thermal degradation by using dry spinning rather than melt spinning.

In addition to retaining polymer molecular weight, non-wovens with high burst and tensile strength can be produced by controlling the formation of the web. Tackiness of the fibers collected at the web can be controlled to improve fusion of the fibers at their crossover points. Unexpectedly high cohesion of the fibers within the dry spun non-woven can be achieved by controlling the stripping rate of the solvent and the tackiness of the fibers during the web collection process leading to improved fusion of the fibers at their crossover points.

With appropriate choice of solution flow rate (ml/min), distance between the nozzle and the collector, needle diameter, needle extrusion distance, temperature, choice of solvent, collection time, polymer molecular weight, and gas (e.g. air) pressure, high burst strength non-wovens comprising fine fibers with average diameters of 0.01 µm to 50 µm can be prepared. For example, dry spun non-wovens of P4HB with a thickness of 0.097 mm can be prepared with a burst strength of 0.47 Kgf using a ⅜" fixture. Increasing the thickness to 0.106 mm can increase the burst strength to 0.75 Kgf.

A. Method of Making P4HB Polymer or Copolymer Non-Wovens by Dry Spinning

In a preferred method, a non-woven of P4HB polymer or copolymer may be prepared as follows. The P4HB polymer is dissolved in a solvent to make a polymer solution. A suitable dry spinning apparatus is shown in FIG. 1. This consists of a nozzle through which the polymer solution is injected into a stream of accelerated gas. A preferred set up comprises compressed air as the source of gas (controlled by a pressure regulator), a REGLO-Z digital pump drive equipped with a suction shoe pump head to control the injection rate of the polymer solution, a spraying apparatus that consists of concentric nozzles, and a rotating mandrel as the collector. Collecting the fibers on a rotating mandrel aligns the fibers substantially in the machine direction. The alignment can be confirmed by SEM images, and by measurements of mechanical properties in each direction of the non-woven. Notably, increasing the rpm of the rotating mandrel results in a steady increase in the alignment, and results in a steady increase in the tensile strength of the non-woven in the machine direction (i.e. rotational direction) relative to the cross direction.

The collector is positioned at a desired fixed distance from the nozzle. The spraying apparatus consists of an inner and a concentric outer nozzle, which creates a low pressure region near the orifice of the inner nozzle. Polymer strands are consistently shot to the collector due to the combination of the low pressure zone and stripping at the solution/gas interface. Solvent evaporates during the time the polymer strand leaves the nozzle and hits the collector due to the high surface to volume ratio of the strands coupled with the high gas turbulence and temperature.

A number of parameters can be varied to control the non-woven thickness, density and fiber sizes including, but not limited to, solution flow rate (ml/min), distance between the nozzle and the collector, needle configuration (including needle diameter and needle extrusion distance), temperature, choice of solvent, polymer molecular weight, polymer concentration in solution, collection time, gas (e.g. air) pressure and speed and/or circumference of the rotating collector plate.

In some embodiments, the speed of the rotating collector plate is 10 rpm. In a preferred embodiment the speed of the rotating collector plate is greater than 50 rpm and more preferably, greater than 100 rpm.

At a collector diameter of 8 cm, a rotational speed of 100 rpm results in a linear speed for the collector surface of approximately 25 m/min or 82 ft/min. The distance between the spray gun nozzle and the rotating collector plate may be adjusted to any desired distance, depending upon the spinning parameters including the pressure of the compressed air, but is preferably between 20 inches and 40 inches. If the rotating collector plate is a cylinder, the diameter and width of the cylinder may be sized appropriately for collection of the nonwoven. The desired size will depend upon the configuration and capacity of the spray gun assembly (which may, for example, comprise a single or multiple nozzles), and the quantity of nonwoven being collected. In an embodiment, the diameter of the rotating cylinder is between 0.25 inches and 6 inches, and the width of the rotating cylinder is between 6 inches and 20 inches. Wider collectors may also be used if a plurality of spray nozzles is used. The time required to collect the nonwoven on the rotating collector plate will depend upon the desired thickness of the nonwoven and configuration of the nonwoven, capacity of the spray gun assembly, concentration of the polymer solution, choice of solvent, temperature, nozzle diameter(s), and the pressure of the compressed air.

B. Method of Making Three-Dimensional P4HB Polymer or Copolymer Non-Wovens by Dry Spinning A particular advantage of the dry spun method described herein over melt blown methods is that non-woven can be spun directly onto scaffolding structures to make three dimensional structures. This is achieved by either positioning the scaffold at the fiber collection plate and rotating the scaffolding structure during fiber collection, or alternatively, rotating the nozzle around the scaffold.

The present invention will be further understood by referenced to the following non-limiting example.

EXAMPLE 1

Preparation of P4HB Non-Woven by Dry Spinning

P4HB (Tepha, Inc., Lexington, Mass.) ($M_w$ 490 kDa) was dissolved in chloroform to make an 8% (wt/vol) polymer solution. P4HB dry spun non-woven was produced as described above, using a stationary fiber glass plate, and the following conditions:
Solution flow rate: 3 mL/min
Distance between nozzle and collector: 32 inches
Needle: 0.035" ID×0.375" extrusion distance
Air pressure: 55 psi
Temperature: Ambient
Collection time: 6 minutes The molecular weight $M_w$ of the dry spun non-woven was determined by GPC relative to polystyrene, and found to be 474 kDa. Therefore the P4HB polymer lost a $M_w$ of only 16 kDa (or approx. 3%) during processing into the dry spun non-woven.

Using methods similar to that described above the following dry spun non-wovens was prepared:

| Reference | Areal Density (g/m$^2$) | Burst Strength (Kgf) (3/8" probe) |
|---|---|---|
| KG02-105-4 | 13.3 | 0.75 |

EXAMPLE 2

Preparation of a P4HB Non-Woven/Chitosan Patch by Dry Spinning

A similar procedure to that described in Example 1 was used to dry spin a P4HB non-woven directly onto a chitosan patch, except that the chitosan patch was placed in the collector position and the distance between the patch and the nozzle was adjusted to 30 inches. Collection times of 1, 2, 4, 6 and 8 minutes were used to make samples.

EXAMPLE 3

Comparison of Dry Spun and Melt Blown Non-Woven Molecular Weights

Several samples of P4HB melt-blown non-woven were prepared according to the procedure of Example 1 of WO 09/085823 to Ho et al. using P4HB with a starting molecular weight ($M_w$) of 328 kDa. The molecular weight (Mw) of the resulting P4HB melt-blown non-wovens was found to be 207 to 157 kDa, representing a 47 to 52% decrease in the molecular weight ($M_w$) of the polymer during processing. This compares to a molecular weight ($M_w$) decrease of just 3% for the dry spun P4HB non-woven produced in Example 1. Thus it is apparent that for any given P4HB polymer resin, production of a non-woven by dry spinning will yield a much higher molecular weight fabric than by melt blowing.

EXAMPLE 4

Preparation of Poly-4-hydroxybutyrate-co-3-hydroxybutyrate Copolymer (PHA3444) Non-Woven by Dry Spinning PHA3444 (Sample ID: DM23.61A, Tepha, Inc., Lexington, Mass.) ($M_w$ 651 kDa, 24% 4-hydroxybutyrate co-monomer) was dissolved in chloroform to make a 12% (wt/vol) polymer solution. PHA3444 dry spun non-woven was produced as described above, using a stationary fiber glass plate, and the following conditions:

Solution flow rate: 32 mL/min
Distance between nozzle and collector: 30 inches
Needle: 0.035" ID×0.375" extrusion distance 40 psi. The results are reported in Table 1 with the ratios of properties in the machine and cross directions (X/Y) calculated for tensile strength.

TABLE 1

Tensile properties of non-woven in the machine direction (X) and cross direction (Y) as a function of mandrel rotation speed.

| Sample ID | rpm of collector | X-direction Thickness (μm) | X-direction Max Load (kgf) | X-direction Max Load per mm Thickness (kgf/mm) | Y-direction Thickness (μm m) | Y-direction Max Load (kgf) | Y-direction Max Load per mm Thickness (kgf/mm) | Ratio (X/Y) Max Load/mm X Max Load/mm Y |
|---|---|---|---|---|---|---|---|---|
| KG05-17-1* | 0 | 169 ± 24 | 0.13 ± 0.03 | 0.77 | 220 ± 13 | 0.17 ± 0.02 | 0.77 | 1.00 |
| KG05-17-2 | 166 (20%) | 298 ± 52 | 0.50 ± 0.10 | 1.67 | 346 ± 19 | 0.19 ± 0.01 | 0.55 | 3.04 |
| KG05-17-3 | 526 (50%) | 237 ± 44 | 0.40 ± 0.10 | 1.68 | 273 ± 8 | 0.14 ± 0.01 | 0.51 | 3.29 |
| KG05-17-4 | 1166 (100%) | 255 ± 21 | 0.44 ± 0.06 | 1.73 | 249 ± 9 | 0.11 ± 0.00 | 0.44 | 3.93 |

Air pressure: 20 psi
Temperature: Ambient
Collection time: 5 minutes

EXAMPLE 5

Preparation of Non-Wovens with Anisotropic Mechanical Properties

The dry spinning apparatus 10 shown in FIG. 1 was assembled and consisted of a solution reservoir 12 containing a solution of P4HB in chloroform, a REGLO-Z digital pump drive 14 equipped with a suction shoe pump head to control the injection rate of the polymer solution, an automatic spraying gun 16 (Model RA 5, Krautzberger GmbH, Germany) using compressed air 18 as the source of gas (controlled by a pressure regulator), and a wax paper covered rotating mandrel 22 (OD: 3.25 inches, width: 14 inches) as the collector. The distance between the spray gun nozzle and the collector was set at 27 inches, and a DC gear motor (Model 7CU24, Dayton Electric Mfg Co, IL) was used to control the speed of the rotating mandrel.

Poly-4-hydroxybutyrate (P4HB) was dissolved in chloroform to make an 8% (wt/vol) solution of the polymer, and the solution was pumped 14 into the dry spinning apparatus at a rate of 0.85 ml/min. Compressed air 18 at a pressure of 40 psi was introduced into the spray gun 16 so that strands 20 of P4HB fiber were sprayed consistently from the spinning nozzle 16 and onto the rotating mandrel collector 22. The solvent evaporates from the fibers during the spraying process and the fibers are collected as a non-woven fabric. The dry spun fibers were collected at the rotating mandrel at different rotational speeds from 166 rpm to 1,166 rpm, and a control sample was collected using a flat fiberglass filter (i.e. stationary plate), see examples in the table below. These different rotational speeds resulted in different speeds for the collector surface, based on the diameter of the collector and its rotational speed.

The collection time was 20 minutes for each sample. After collection, strips of the non-woven samples were cut (0.5 inch×3.0 inch), the thickness of each non-woven sample was measured in the machine and cross directions, and the tensile properties measured using an Instron MINI 55 Tensile Tester at a crosshead speed of 250 mm/min with a grip pressure of As is evident from the results, the tensile strength in the machine direction (X-direction) increased as the speed of the mandrel was increased, while it decreased in the cross direction (Y-direction) with increasing speed of the mandrel. Accordingly, the ratio of tensile strength in the machine direction to that in the cross direction (X/Y) increased from 1.0 when non-woven was collected at a stationary plate to 3.9 when the non-woven was collected on a mandrel rotating at 1166 rpm.

SEM images of each of the four samples listed in Table 1 were compared to samples collected on a stationary plate. Samples showed a random configuration of the dry spun fibers when the non-woven was collected at a stationary plate. A more ordered and aligned structure was obtained when the non-woven was collected on the mandrel rotating at 166 rpm. At a mandrel rotation speed of 526 rpm, a much more significant alignment of the P4HB dry spun fibers. At a mandrel rotation speed of 1166 rpm the dry spun fibers were substantially aligned in the machine direction.

Preliminary measurements by DSC indicate that the increase in mechanical properties is due to alignment of the fibers in the machine direction rather than as a result of orientation of the fibers (i.e. there is no significant increase in the melting temperature of the polymer as a result of dry spinning onto a rotating mandrel which would be expected if there was significant orientation of the fibers).

EXAMPLE 6

Fiber Size and Burst Strength of Non-Wovens with Anisotropic Mechanical Properties P4HB non-wovens were prepared as in Example 5 using a stationary collector and a rotating collector at speeds from 166 to 1166 rpm. The samples were imaged using SEM and the fiber diameters were measured using ImageJ software against a calibrated silicon sizing standard. Ball burst strengths of the samples were measured using a 3/8" ball burst fixture. The data are shown in Table 2. As can be seen in the Table, the collector speed did not have a substantial impact on the fiber diameters. The data indicates the fibers did not undergo any substantial necking or orientation during the spinning process. Additionally, the ball burst strengths of the non-woven materials were not substantially affected by the collector speeds. There were differences in the thickness and ball burst strength values for the non-wovens, however, when burst strength was normalized for mesh thickness, the burst strength per unit thickness was very similar for all the samples tested and was independent of the collector speed and degree of fiber alignment.

TABLE 2

Properties of P4HB dryspun scaffolds (random vs aligned)

| Sample ID | Speed of collector (rpm) | Fiber diameter* (μm) | Thickness (μm) | Ball burst strength (kgf) (⅜" fixture) | Strength/Thickness** (kgf/μm) |
|---|---|---|---|---|---|
| KG05-28-1 | 0 | 1.87 ± 1.16 | 107 ± 21 | 0.421 ± 0.084 | $3.93 \times 10^{-3}$ |
| KG05-28-2 | 166 (20%) | 1.90 ± 1.54 | 239 ± 56 | 0.999 ± 0.274 | $4.18 \times 10^{-3}$ |
| KG05-28-3 | 526 (50%) | 1.81 ± 1.41 | 214 ± 52 | 0.914 ± 0.251 | $4.27 \times 10^{-3}$ |
| KG05-28-4 | 1166 (100%) | 1.76 ± 1.11 | 188 ± 47 | 0.779 ± 0.220 | $4.14 \times 10^{-3}$ |

*Fiber diameter was measured by ImageJ (108 fibers were chosen randomly and measured)
**Five specimens were tested for each sample.

EXAMPLE 6

Comparative Example of Non-Woven Produced by Melt Blowing

The ratio of tensile strength in the machine and cross directions of ten non-woven samples produced by the melt blowing method described in Example 1 of U.S. Pat. No. 8,287,909 to Martin et al. were measured in order to determine whether the non-woven produced by melt blowing has anisotropic mechanical properties. The average tensile strength in the machine direction was found to be 3.5627 kgf. In the cross direction, the average tensile strength was found to be 3.5679 kgf. The ratio of tensile strength in the machine direction versus the cross direction was therefore approximately 1.00 indicating that the melt-blown non-woven produced by Example 1 of U.S. Pat. No. 8,287,909 does not have anisotropic properties.

Modifications and variations of the methods and compositions will be apparent from the foregoing detailed description and are intended to come within the scope of the appended claims.

We claim:

1. A non-woven device comprising dry spun fibers of poly-4-hydroxybutyrate or copolymer thereof wherein the ratio of the tensile strength in the machine direction to the tensile strength in the cross direction is greater than 1.2.

2. The non-woven of claim 1 wherein the non-woven is made by dry spinning and collected on a rotating plate, cylinder or mandrel.

3. A non-woven device comprising dry spun fibers of poly-4-hydroxybutyrate or copolymer thereof, wherein the weight average molecular weight of the poly-4-hydroxybutyrate or copolymer thereof decreases less than 20% during the processing of the polymer or copolymer.

4. The non-woven of claim 1 wherein the non-woven is formed into a device or is a component of a device selected from the group consisting of stent, stent graft, stent coating, drug delivery device, device for temporary wound or tissue support, repair patch, tissue engineering scaffold, retention membrane, anti-adhesion membrane, tissue separation membrane, hernia repair device, hernia mesh, hernia plug, laminated knitted or woven device, device coating, cardio-vascular patch, vascular closure device, sling, device for pelvic floor reconstruction, bladder repair device, biocompatible coating, rotator cuff repair device, meniscus repair device, adhesion barrier, guided tissue repair/regeneration device, articular cartilage repair device, nerve guide, tendon repair device, ligament repair device, rotator cuff device, meniscus repair device, articular cartilage repair device, osteochondral repair device, intracardiac septal defect repair device, atrial septal defect repair device, PFO (patent foramen ovale) closure device, left atrial appendage (LAA) closure device, pericardial patch, bulking agent, filling agent, vein valve, heart valve, vascular graft, myocardial regeneration device, anastomosis device, bone marrow scaffold, meniscus regeneration device, ligament and tendon graft, ocular cell implant, spinal fusion device, imaging device, skin substitute, dural substitute, bone graft substitute, wound dressing, bandage, wound healing device, burn dressing, ulcer dressing, skin substitute, hemostat, plastic surgery device, breast lift device, mastopexy device, breast reconstruction device, breast augmentation device (including devices for use with breast implants), breast reduction device (including devices for removal, reshaping and reorienting breast tissue), devices for breast reconstruction following mastectomy with or without breast implants, facial reconstructive device, forehead lift device, brow lift device, eyelid lift device, face lift device, rhytidectomy device, thread lift device (to lift and support sagging areas of the face, brow and neck), rhinoplasty device, device for malar augmentation, otoplasty device, neck lift device, mentoplasty device, cosmetic repair device, and device for facial scar revision.

5. The non-woven of claim 1 further comprising a second polymer selected from the group consisting of a polymer of glycolic acid, lactic acid, 1,4-dioxanone, trimethylene carbonate, caprolactone and combinations thereof.

6. The non-woven of claim 1 further comprising additives selected from the group consisting of prophylactic agents; diagnostic agents, and therapeutic agents.

7. The non-woven of claim 1 further comprising additives selected from the group consisting of plasticizers, nucleants, compatibilizers, porogens, radiolabelled substances, imaging agents, radiopaque markers, contrast agents, anti-oxidants, dyes, viscosity modifiers, and odor control agents.

8. A method of making a dry spun non-woven comprising a poly4-hydroxybutyrate homopolymer or copolymer, wherein the ratio of the tensile strength in the machine direction to the tensile strength in the cross direction is greater than 1.2 comprising collecting polymeric fibers using a rotating collector plate or cylinder, wherein the speed and circumference of the rotating collector plate is varied to select the properties desired in the machine direction relative to the cross direction.

9. The method of claim 8 wherein the polymer is pumped as a solution through a spray gun nozzle.

10. The method of claim 8 wherein the rotating collector plate or cylinder speed is at least 10 rpm, 50 rpm, or greater than 100 rpm.

11. The method of claim 9 wherein the distance between the spray gun nozzle and the rotating collector plate or cylinder is between 20 inches and 40 inches.

12. The method of claim 8 wherein the polymer is spun onto a rotating collector cylinder having a diameter between 0.25 inches and 6 inches and a width of between 6 inches and 20 inches.

13. The method of claim 8 wherein the polymer solution consists of poly 4-hydroxybutyrate.

14. A method of using the non-woven of claim 1 in medical applications as a non-woven polymeric device.

15. The method of claim 14 comprising inserting or implanting the non-woven device into an individual in need thereof.

16. The method of claim 15, wherein it is used for the repair, regeneration or replacement of soft tissue.

17. The method of claim 15 wherein the device comprises a therapeutic, prophylactic or diagnostic agent.

* * * * *